United States Patent [19]
Leonard

[11] Patent Number: 5,431,630
[45] Date of Patent: Jul. 11, 1995

[54] NEEDLE GUARD AND NONREUSABLE SYRINGE

[75] Inventor: Robert J. Leonard, Lynnfield, Mass.

[73] Assignee: Surgic-Acid, Inc., South Walpole, Mass.

[21] Appl. No.: 86,651

[22] Filed: Sep. 7, 1993

[51] Int. Cl.$^6$ .............................................. A61M 5/00
[52] U.S. Cl. .................... 604/110; 604/192; 604/195; 604/198; 604/199; 604/263
[58] Field of Search ............... 604/110, 192, 195, 198, 604/199, 263

[56] References Cited

U.S. PATENT DOCUMENTS

| | | | |
|---|---|---|---|
| 4,093,709 | 6/1978 | Choi et al. | 424/19 |
| 4,346,709 | 8/1982 | Schmitt | 128/260 |
| 4,351,825 | 9/1982 | Sothmann et al. | 424/19 |
| 4,452,775 | 6/1984 | Kent | 424/19 |
| 4,591,496 | 5/1986 | Cohen et al. | 424/15 |
| 4,657,535 | 4/1987 | Nishimura et al. | 604/263 |
| 4,702,738 | 10/1987 | Spencer | 604/198 |
| 4,801,295 | 1/1989 | Spencer | 604/198 |
| 5,026,345 | 6/1991 | Teringo | 604/110 |
| 5,108,378 | 4/1992 | Firth et al. | 604/192 |
| 5,205,824 | 4/1993 | Mazur | 604/110 |
| 5,267,962 | 12/1993 | Jenson | 604/195 |
| 5,279,581 | 1/1994 | Firth et al. | 604/198 |

Primary Examiner—C. Fred Rosenbaum
Assistant Examiner—N. Kent Gring
Attorney, Agent, or Firm—Wolf, Greenfield & Sacks

[57] ABSTRACT

A non-reusable syringe is disclosed, as well as a needle guard for use in the syringe. The needle guard is a chamber for enclosing a syringe needle and has a heat-labile material disposed on a surface thereof. The heat-labile material can melt and flow onto the needle when heated and, when cooled, the material will solidify and encapsulate the needle within the chamber.

A syringe for use with the needle guard has a needle that is retractable inside the syringe body.

15 Claims, 7 Drawing Sheets

NEEDLE GUARD AND NONREUSABLE SYRINGE

FIELD OF THE INVENTION

This invention relates to a needle guard and syringe for preventing inadvertent needle punctures or sticks and for disabling the syringe.

BACKGROUND OF THE INVENTION

In light of widespread abuse of syringes and needles by drug addicts, and the spread of AIDS and other infectious diseases associated with the use of contaminated needles, many methods for preventing syringe and/or needle reuse have been proposed.

For example, used syringes and needles have been disposed of by cutting the needles or by melting and burning the syringes. These methods are not entirely satisfactory because the syringes and needles are not rendered completely useless immediately after their first use. This provides an opportunity for individuals to reuse the syringe and needle assemblies. Moreover, accidental puncture of the skin of health care workers who are involved in manipulating and disposing needles and syringes has been a serious problem.

Although other methods have been developed for preventing the reuse of syringes, mechanical devices and are often too complicated for ordinary individuals to use. Furthermore, the complexity of the nonreusable syringes makes them rather costly to manufacture.

SUMMARY OF THE INVENTION

The present invention is directed towards a needle guard for rendering a needle or needle syringe assembly inoperative. The needle guard is an elongated member that has a bore for receiving a needle. The member has at least a portion formed from a heat-labile material for surrounding at least part of the needle. In one embodiment, the needle guard is an elongated non heat-labile core and the heat-labile material is disposed on at least one surface of the core. The heat-labile material is preferably disposed on an inner surface of the core, and is most preferably disposed on both inner and outer surfaces of the core. The heat-labile material melts when the needle guard is heated to at least 30° C. and flows onto the needle. Once cooled, the heat-labile material solidifies around the needle within the needle guard and encapsulates the needle.

The syringe of the invention has a hollow body, a plunger operating within the body, and a syringe needle affixed to a resilient hub located within the hollow body. The hub is normally seated immediately adjacent a discharge end of the syringe body but can be displaced within the syringe body. The syringe body is constructed and arranged to permit the needle guard to penetrate into the syringe body in order for the needle guard to directly contact the hub. The needle guard can be inserted into the syringe body by forcing the syringe downward or the hub upward; thus causing the needle to retract into the syringe body.

The invention also pertains to a method for disabling a syringe. The method includes the steps of providing a needle guard having an elongated chamber arranged to receive a needle, the chamber formed from a heat-labile material; engaging the needle guard with the needle to fully enclose it; heating the needle guard a temperature sufficient to melt the heat-labile material, thereby causing it to flow onto the needle, and cooling the guard, thereby encapsulating the needle within the solidified heat-labile material of the needle guard.

The invention also pertains to a kit for disabling a syringe. The kit includes the needle guard of the invention and a heat-conductive template constructed and arranged to engage with a portion of the needle guard in a heat conductive relationship. When the template is heated, the heat labile material melts and flows onto the needle. When cooled, the heat-labile material encapsulates the needle within the needle guard.

Another embodiment of the kit includes the needle guard of the invention, a heat-conductive template and a syringe of the invention having a displaceable hub located within the syringe body. The syringe body is constructed and arranged to permit the needle guard to be inserted into the syringe body so that it contacts the hub, thus displacing the needle into the syringe body.

It is an object of the invention to provide a needle guard for incapacitating a needle and/or syringe.

It is a further object of the invention to provide a non-reusable syringe.

Other objects and features of the present invention will become apparent from the following detailed description, when taken in connection with the accompanying drawings which disclose multiple embodiments of the invention. It is to be understood that the drawings are designed for the purpose of illustration only and are not intended as a definition of the limits of the invention.

DETAILED DESCRIPTION OF THE INVENTION

The present invention pertains to a nonreusable syringe and to a needle guard designed to enclose a hypodermic needle. The term "needle" describes those objects that are 18 gauge or less. Needles bigger than 18 gauge are often referred to as "cannulas". Nevertheless, as used in this specification, the term "needle" is intended to include cannulas over 18 gauge.

Needles used with the apparatus of the present invention may be made of stainless steel, carbon steel, chromium, nickeloid, platinum, platinum-iridium, silver or gold. Needles used with the present apparatus may also have many different uses, such as for local anesthesia, aspiration, subcutaneous administration or for any of various special purposes that should be appreciated by those of ordinary skill in the art. The usual range of needle diameter is from 13 gauge to 27 gauge. Needles useful with the apparatus of the present invention are seldom less than 0.25 inches long or longer than approximately 3.5 inches. Special needles useable with the invention include biopsy and bone marrow transfusion needles ranging from 16–19 gauge and about 0.5 to 3.5 inches long. Needles for local anesthesia range from about 20 gauge (0.5 inches) to 26 gauge. Intravenous, blood transfusion needles range from about 15 gauge (1.25 inches) to 19 gauge (2.5 inches).

The needle guard of the invention is provided with a heat-labile material that can encapsulate a needle or a portion thereof. The term "heat-labile" refers to a material that melts upon application of heat and changes state from a solid phase to substantially a liquid or a gelatinous phase. When the heat-labile material is subsequently cooled, it reverts back into a solid phase.

The term "encapsulate" refers to any process which causes the heat-labile material of the needle guard to physically surround the needle. The term includes not only chemical bonding between the needle and the heat-labile material, but also to a purely physical adhesion between the heat-labile material and the needle. This physical adhesion is enhanced if at least a portion of the needle is porous and/or does not have a smooth surface, so that the heat-labile material of the needle guard infiltrates the interstices, pores and/or irregularities of the needle material.

The needle guard of the invention is an elongated member having a bore (i.e. a chamber) constructed to receive a needle, which needle is either isolated, or attached to a syringe. This elongated member can be made entirely of a heat-labile material, or can be made of a heat-labile material in combination with a non heat-labile material, such as a plastic, that provides structural rigidity to the member. Preferably, however, the elongated member is a core of heat-conductive material, having a heat-labile material disposed on one surface of the core, as described in more detail below. The core transfers heat energy necessary to melt the heat-labile material.

Figure 1:
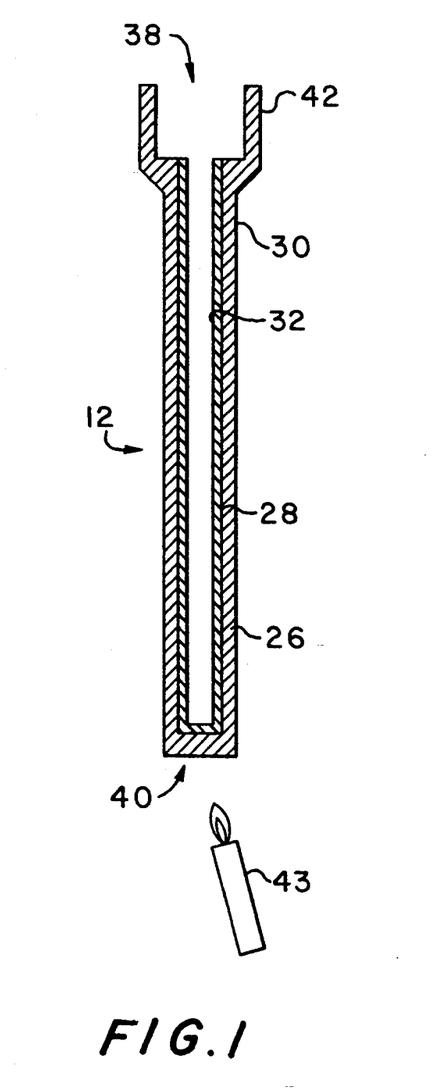
FIG. 1 is a front view of the needle guard of the first embodiment

FIG. 1 shows a preferred needle guard 12, comprising a heat-conductive core 26 having an inner surface 28 and an outer surface 30. Although core 26 preferably is made of a heat conductive material such as stainless steel or copper, less heat-conductive materials may be used such as a ceramic material, provided that sufficient heat is transferred through the core to melt the heat-labile polymer at a predetermined temperature. The minimum melting temperature of the heat-labile material is preferably just above ambient temperature (i.e. about 30° C.) in order to prevent inadvertent melting of the material during storage in heated areas.

In FIG. 1, the inner surface of the core supports a layer of heat-labile material 32. This heat-labile material is preferably a polymer, and is most preferably a biodegradable polymer that can be selected from a variety of well-known compounds. Biodegradable polymers include hydrocarboxylic acids, especially lactic acid and glycolic acid, polycaprolactone and copolymers thereof. For example, various proportions of lactide and glycolide can be used as the heat-labile material, such as 50/50, 65/35, 75/25, and 85/15 percent weight ratios of poly (DL-lactide-co-glycolide). In addition, substantially 100% weight percent poly (DL-lactide), poly (L-lactide), and polyglycolide can be used. Bioerodible polymers of this type are available from Birmingham Polymers, Inc. of Birmingham, Alabama 35222. Copolymers of gluconic acid and ethyl-L-glutamic acid and other polypeptides can also be used, as well as poly(orthoesters) (described in U.S. Pat. No. 4,093,709 issued to Choi et al.) and poly(orthocarbonate) (U.S. Pat. No. 4,346,709 issued to Schmitt). Also, poly(acrylate) materials can be employed, such as copolymers of acrylic and methacrylic acid esters or copolymers of methacrylic acid and methyl methacrylate (Sothmann et al., U.S. Pat. No. 4,351,825). Cholesterol and ethylene vinyl acetate copolymers can also be used. See for example, U.S. Pat. Nos. 4,452,775 (J. S. Kent) and 4,591,496 (J. M. Cohen et al.), respectively. Each cited patent is incorporated herein by reference.

Although the needle guard 12 has an open end 38 and closed end 40 illustrated in FIG. 1, the needle guard can be open at both ends.

Figure 2:
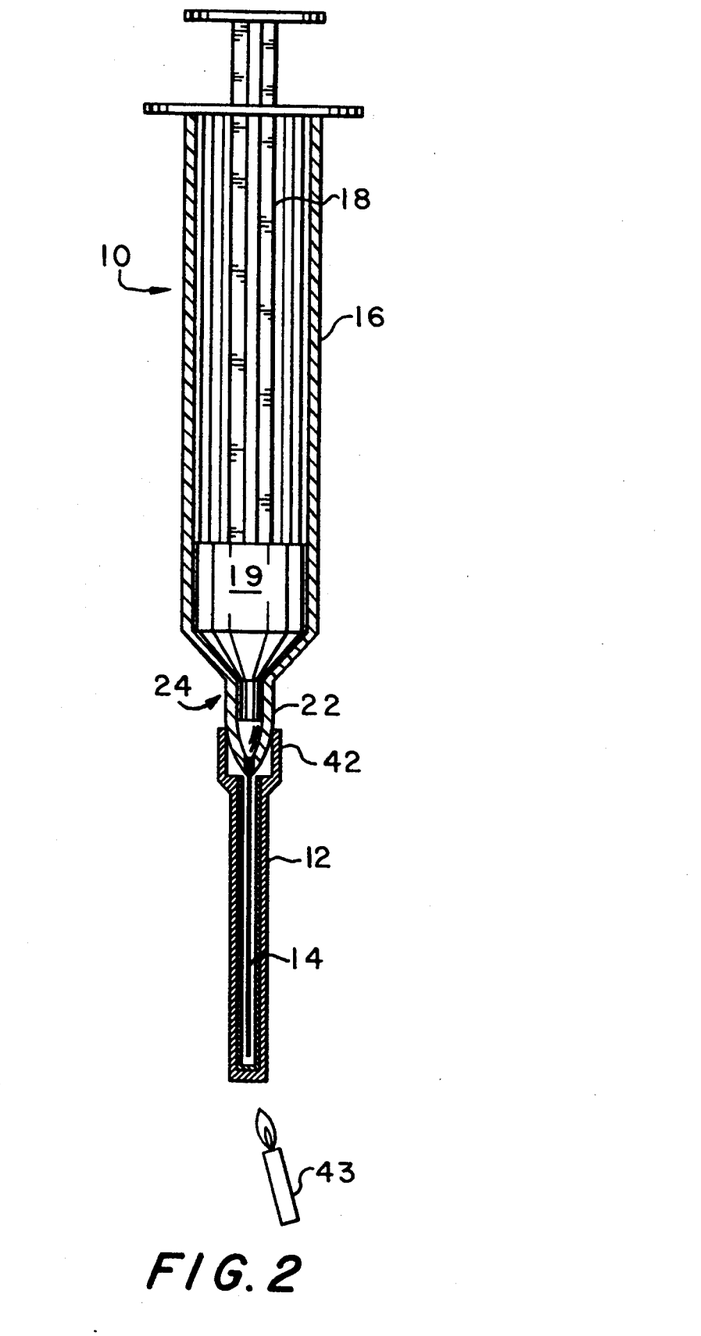
FIG. 2 shows a syringe, needle, and needle guard assembly with a needle guard of the first embodiment.

FIG. 2 shows a syringe 10 with the needle guard 12 of FIG. 1, placed on a syringe needle 14. The syringe 10 includes a syringe body 16, a plunger 18 having a plunger tip 19 operating within the syringe body, and a needle locking mechanism 22 that prevents the needle 14 from being easily removed from the syringe body. Needle 14 joins syringe body 16 at a discharge end 24 of syringe body 16. The term "discharge end" refers to the distal end of the syringe body having an orifice through which fluid from the syringe is removed into the environment of use. Syringe needle locking mechanism 22 preferably includes Luer-type or other lock systems that engages a portion of the syringe with a portion of the needle. Other arrangements for attaching the needle to the syringe are contemplated, as would be apparent to those of ordinary skill in the art.

In FIG. 2, the needle guard 12 is attached to the syringe body 16 at the discharge end 24 of the syringe. This may be accomplished by an expanded member 42 on the needle guard, which member is supported on needle locking mechanism 22. The expanded member 42 can include a flange that engages a portion of locking mechanism 22 in a press-fit or frictional manner.

In another embodiment (not illustrated) expanded member 42 is not required because the guard is attached to the syringe/needle assembly in a friction fit between the needle and the immediately adjacent heat-labile layer 32. Because of this frictional fit, the needle guard can receive only part of a needle. That is, in this non-illustrated other embodiment, the needle guard of FIG. 1 can enclose the needle only at the needle tip. This configuration is not, however, the most preferred one since any liquid contaminant adhering to the needle above the tip is not encapsulated. Thus, a needle guard that receives the entire length of the needle is preferred.

Figure 3:
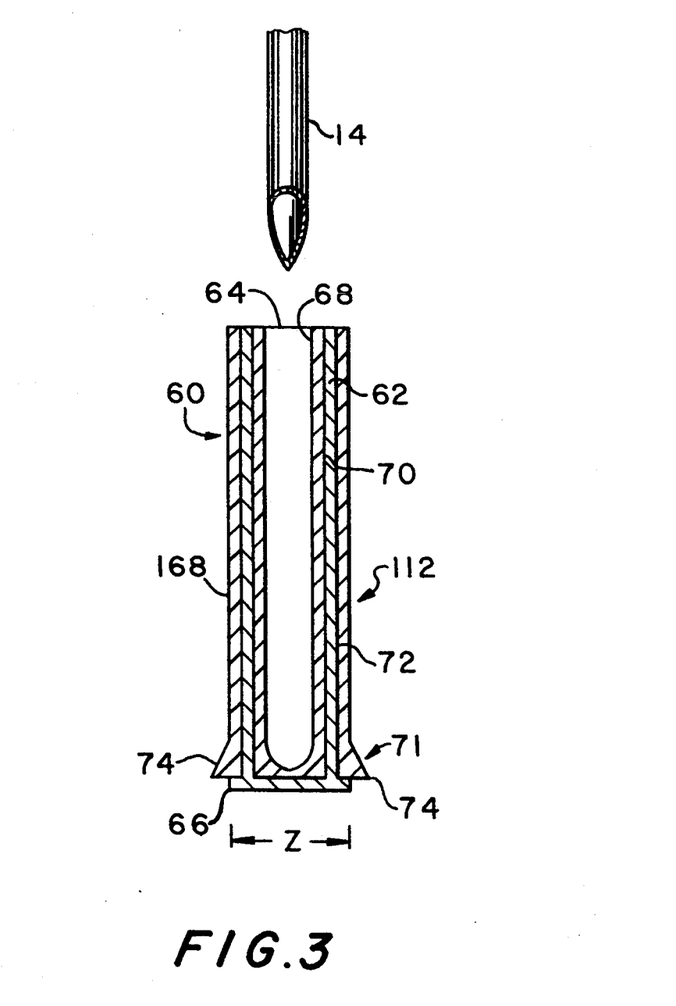
FIG. 3 is a front view of the needle guard of the second embodiment.
Figure 4:
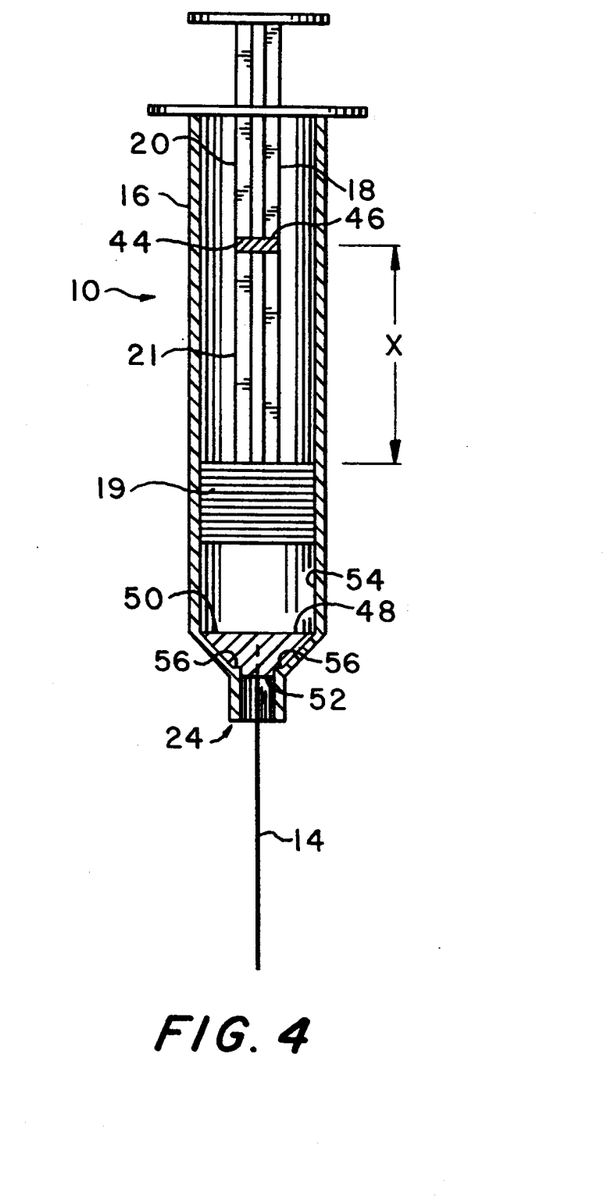
FIG. 4 shows a syringe and needle assembly for use with a needle guard of the second embodiment.

FIG. 3 illustrates a needle guard 112 designed to be used with a different type of syringe, the syringe illustrated in FIG. 4. The needle guard 112, of a defined outside diameter Z, is a substantially hollow elongated member 60 having a bore constructed to receive a needle 14. The member 60 includes a core 62 that is preferably cylindrical and has an open end 64 and a closed end 66. Both the core 60 and closed end 66 are fabricated of a heat-conductive material that is preferably a heat-conductive metal and is most preferably stainless steel. A layer of heat-labile material 68 is disposed on an inner peripheral surface 70 of core 62 and a second layer of heat-labile material 168 is disposed on an outer peripheral surface 72 of the core. On opposite sides of the distal end 71 of needle guard 112, the peripherally disposed layer of heat-labile material 168 forms a pair of outward, radially extending shoulders 74. Shoulders 74 are constructed and arranged to engage with detents 56 formed on the inner surface of the discharge end 24 of the syringe body 16 (see FIG. 4).

FIG. 4 shows a syringe that is to be used with the needle guard 112 of FIG. 3. The syringe includes a hollow body 16 and a plunger 18 disposed within the body, the plunger terminating in a plunger tip 19. Plunger 18 has two parts 20 and 21, that are joined by a frangible joint 44 located some distance (X) proximal to the plunger tip 19. Frangible joint 44 is substantially orthogonal to the long axis of the plunger 18. Preferably, joint 44 is a thin layer of silicone or other adhesive 46 that joins adjacent parts 20 and 21 of plunger 18. The adhesive resists forces in a direction parallel to the needle 14 and syringe body 16 but is susceptible to any force that is applied at substantially right angles to plunger 18.

A resilient hub 48 is disposed within the syringe body 16 immediately adjacent the discharge end 24 of the syringe. The hub can be made of any elastomeric material, such as natural or synthetic rubbers, etc. A syringe needle 14 is firmly affixed to hub 48. The needle 14 is affixed to hub 48 by insertion of a portion of the needle directly into the resilient material of hub 48. Lateral pressure exerted orthogonal to the axis of the needle by the force of the hub 48 against the inner walls 54 of the syringe prevents the needle from piercing entirely through hub 48. In addition, the presence of fluid in the syringe body 16 and the combined downward pressure exerted by plunger tip 19 and fluid also keeps the needle fixed in place within the hub.

In the embodiment illustrated in FIG. 4, hub 48 has a proximal face 50 and a distal face 52. The hub is sufficiently resilient to conform to the shape of the inner walls 54 of the syringe body. Hub 48 is designed to sealingly engage with the inner wall 54 of the syringe body 16 so that any material that is to be injected does not leak out into the environment of use between the hub 48 and the inner surface of the syringe body 54. In FIG. 4 proximal face 50 of resilient hub 48 is wider than distal face 52 because of the taper shown in the syringe body. It will be readily appreciated that other configurations of syringe body 16 and hub 48 can be used without departing from the scope of the invention.

The discharge end of the syringe 24, has a bore with an inside diameter Y through which the needle 14 protrudes. The bore diameter Y (shown in FIG. 5) is substantially identical to the outside diameter (Z) of the needle guard (see FIG. 3).

The inner wall of syringe body 16 has a pair of detents 56 disposed on opposite sides of the inner surface 54 at the discharge end 24. Detents 56 are designed to engage with corresponding shoulders 74 in the needle guard 112, that are illustrated in FIG. 3.

Figure 5:
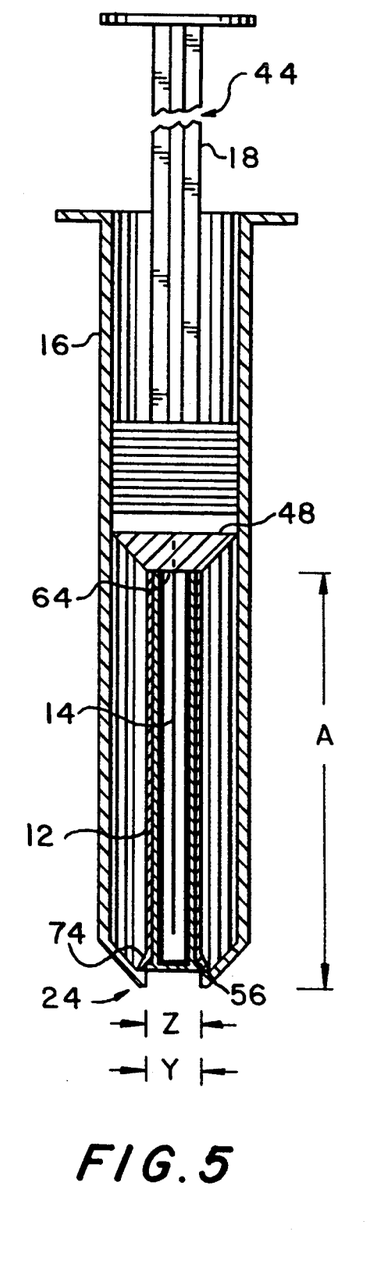
FIG. 5 shows the syringe assembly and needle guard of the second embodiment in an engaged configuration.

FIG. 5 illustrates the engagement of needle guard of FIG. 3 and syringe of FIG. 4 in a manner that allows the syringe to be fully disabled. All reference numbers are identical except where otherwise noted. The needle guard 112 has an outside diameter Z that is substantially identical to the inside diameter Y of the bore in the discharge end 24 of the syringe. Needle guard 112 is shown fully inserted into the discharge end 24 of the syringe, full insertion resulting from engagement of hub 48 with open end 64 of needle guard 112, discussed below.

The resilient hub 48 is adapted for movement between a first position, where the hub is constrained within the discharge end (FIG. 4), and a second position (FIG. 5) where the hub is spaced a distance A from the discharge end 24. The distance A moved by hub 48 is equal to the length of the insertable needle guard 12. As illustrated in FIG. 5, when the needle guard 112 is fully inserted into the syringe, shoulders 74 on the needle guard 112 engage with detents 56 and this locks the closed end of the needle guard into position at the discharge end 24 of the syringe body. Hub 48 is retracted to its maximal extent and, in this position, needle 14 is fully withdrawn into the syringe body 16, thus disabling the needle completely. Moreover, frangible area 44 on plunger 18 can be used to snap off the plunger once the needle is fully retracted inside the syringe body. This effectively prevents any further movement of the needle guard and needle by completely disabling the plunger.

As discussed above, the dimensions of the needle guard of this invention will necessarily vary depending upon the size of the various syringes and needles with which it is used. For a conventional, disposable syringe (see FIG. 2) having a capacity of 10 ml and using a 5 cm long, 22 g needle, the length of an exemplary needle guard would be 5–7 cm. The outside diameter would be 1–3 mm with an inner diameter of 0.5–2 mm. The thickness of the heat-labile layer can range from approximately 0.2 mm. to 2.0 mm.

The needle guard of FIG. 3 is constructed and arranged to be wide enough to penetrate the syringe body of FIG. 4. These dimensions will also vary and a determination of particular sizes is well within the design capabilities of those of ordinary skill in the art.

Generally, the method of disabling a needle assembly through the use of a needle guard of this invention, includes inserting a needle into the needle guard of the invention, which needle guard includes an elongated member comprising a heat-labile material arranged to enclose the needle. Preferably, the chamber includes a core having a heat-labile material supported on at least an inner periphery of the core. Next, the guard is heated to a temperature and for a time sufficient to melt the heat-labile material. Subsequent heating of the heat-labile material allows it to flow onto the needle. The guard is next cooled to allow the heat-labile material to solidify and encapsulate the needle within the member. The time needed to melt the heat-labite material and the conditions under which solidification occurs can easily be determined by those of ordinary skill in the art. Melting temperatures of heat-labile materials described herein are well-characterized.

A method for disabling the syringe embodied in FIG. 4 includes engaging the needle of the syringe with needle guard of this invention, which needle guard includes an elongated member comprising a heat-labile material arranged to enclose the syringe needle. Preferably, the member includes a heat-conductive core having a heat-labile material disposed on both an inner and outer surface of the core. The end of the needle guard nearest the discharge end of the syringe is then inserted into the needle and comes into contact with the resilient hub. The syringe body is pressed downward toward the needle guard. This movement forces the hub to move from its first position, where the hub is constrained at the discharge end, to its second position, where the hub is spaced apart at some distance from the discharge end, thus retracting the needle guard into the syringe body. If a frangible joint is provided in the plunger, this joint can be manipulated to break off the plunger so that the plunger is also disabled. The syringe guard is then heated in order to melt the heat-labile material.

Figure 6A:
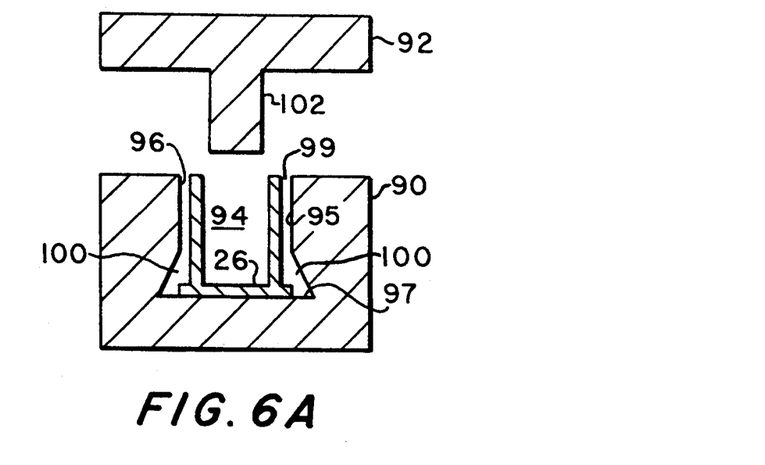
FIGS. 6A–6C illustrate the apparatus and method for forming a needle guard of the invention.
Figure 6B:
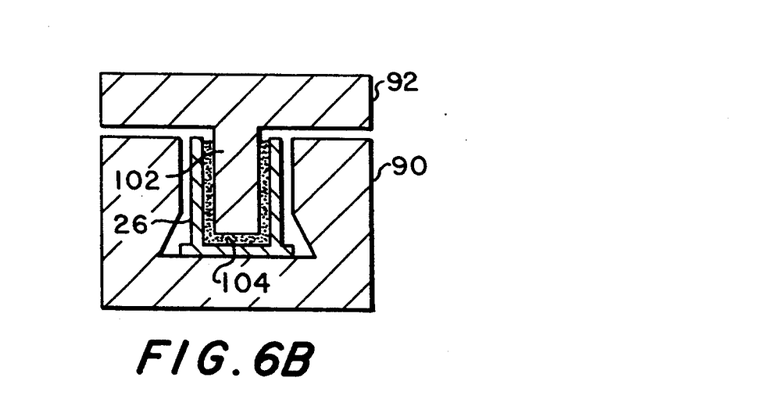
Figure 6C:
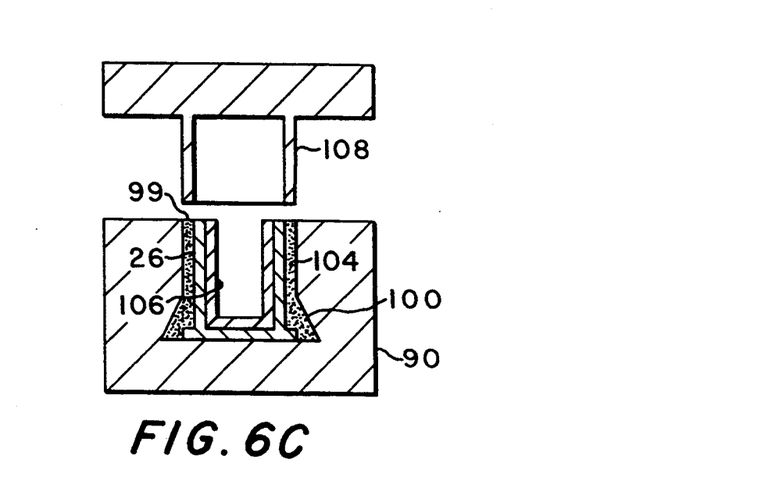

The needle guards 12 and 112 of the invention are manufactured using the apparatus and process illustrated in FIG. 6. The assembly includes at least a bottom block 90 and a top block 92. The blocks have substantially flat facing surfaces so that they may be positioned in face-to-face relationship with respect to one another. The bottom block 90 has at least one cavity 94 with vertical walls 95 and upper 96 and lower 97 edges extending at least partially through the bottom block. The cavity 94 can have a variety of configurations but in the figure illustrated, it is substantially cylindrical throughout its entire length except for wing-like extensions 100 extending radially outward from inner vertical wall 95 near the lower edge 97 of the cavity. These wing-like extensions provide a means for forming the shoulder 74 on the syringe guard, as illustrated in FIG. 5 and explained in more detail below. The cavity 94 preferably has a smooth surface and is lined with a non-stick material such as polytetrafluoroethylene (Teflon ®).

The top block 92 has a pin 102 extending normal to a downwardly facing surface of the top block. Preferably, pin 102 is lined with Teflon ® and is sized and shaped to fit within the cylindrical cavity, as discussed below.

In a preferred embodiment, the entire assembly is made of stainless steel except for the Teflon ® linings of the cylindrical core and pin.

To form a needle guard according to the invention, a stainless steel core 26 (see also FIG. 2) is inserted into the cavity 94 of the bottom block 90. The cavity 94 of the bottom block is constructed and arranged to be larger than an outside diameter of the stainless steel core 26 as shown in FIG. 6A–6C. The stainless steel core 26 is sized and shaped to fit within the cavity 94 of the bottom block so that an annular space 99 is formed between an outside periphery of the stainless steel core 26 and the inner wall 95 of the cavity (FIG. 6A).

A powdered, heat-labile polymer 104 is dispensed into the stainless steel core, as shown in FIG. 6B. The entire assembly is then heated in an oven until the powdered heat-labile material is capable of flowing (i.e. the glass-transition phase). Then, the top 92 and bottom 90 blocks are assembled in face to face relationship. The top block 92 is gently pressed downwards. The Teflon ® lined pin 102 is sized and shaped to fit within the stainless steel core. The pin is thus guided into the open end of the stainless steel core and the heat-labile material is caused to flow between the pin and the stainless steel core (FIG. 6B). Because of the close fit between the pin 102 and the stainless steel core 26, the flowable heat-labile polymer then is compressed into a thin walled tube as the top block 92 is brought into face to face relationship with the bottom block 90. Once the bottom block and top block have been brought into this relationship, the assembly may be removed from the oven and allowed to cool. The pin may then be removed leaving a thin sleeve or coating of heat-labile material 106 within the stainless steel core 26 (FIG. 6C). At this point, the stainless steel core may be removed and can be used as a syringe needle guard for the syringe embodiment, as illustrated in FIGS. 1 and 2.

However, the process can be continued to fabricate a syringe needle guard containing shoulders 74 as mentioned previously. In this situation, powdered heat-labile polymer 104 is next dispensed into the annular space 99 created between an outer periphery of the stainless steel core and the inner wall 95 of the Teflon ®-lined cavity. A second pin 108 is guided into this annular space (FIG. 6C). The entire assembly is then heated until the powdered heat-labile polymer flows. By gently pressing the second pin 108 downwards, the sheath material is caused to flow into the annular space 99 created between the cavity and the core 76, including the outwardly extending radial extensions 100 of the annular space. Because of the close fit between the stainless steel core and the Teflon ® lined cavity, the flowable polymer is compressed into a thin walled tube having the desired outwardly extending portions.

Preferably, the heating process is carried out in an oven. The oven may be an aluminum block containing individual heating chambers sized to receive the block assembly. Heat thus is applied to raise the temperature near the glass-transition temperature of the heat-labile polymer. The temperature is easily determined by those of ordinary skill in the art and under many circumstances, this temperature will be on the order of about 45°. At this temperature, the polymer begins to get tacky and begins to exhibit flow properties.

Referring again to FIG. 1, a schematic illustration is provided of a device 43 for heating the needle guard in order to disable a needle and/or syringe. It will be appreciated that this heating device can be used when the needle is isolated from a syringe or when the needle 14 is affixed to syringe body 16 (see FIG. 2). Heating device 43 can include any heat-producing mechanism provided that the temperature is sufficient to cause the heat-labile material to melt. The heating device 43 can include an infrared source, hotplate, heating tape, heat gun, hot oil bath, hot water bath, microwave source, forced hot air, and the like. Device 43 is not meant to limit the scope of the invention in any way.

Figure 7:
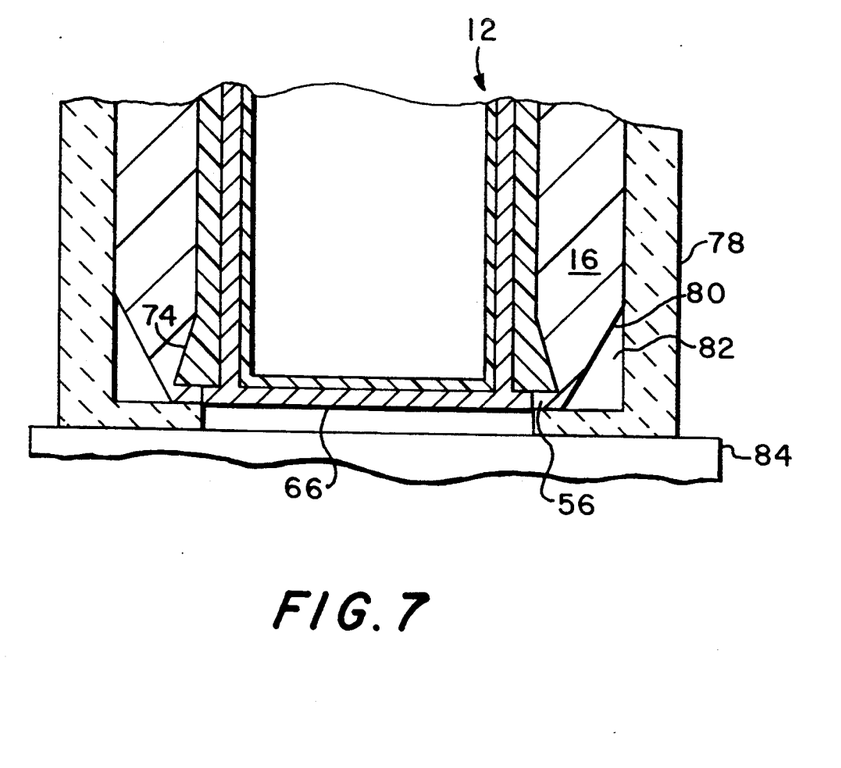
FIG. 7 is a partial view of a heat-conductive template of the invention engaged with the needle guard of the second embodiment.

A preferred method of heating the needle guard to disable a syringe and/or needle is to use a heat-conductive template that can be sealingly engaged with a closed end of the needle guard. FIG. 7 illustrates in partial view one embodiment of a heat-conductive template 78 that can be used with a needle or syringe. The template 78 is preferably made of heat-conductive material such as ceramic and is constructed and arranged to engage simultaneously with: (i) an outer surface 80 of the syringe body 16 at the discharge end; and (ii) the closed end 66 of the needle guard 12. In the particular embodiment illustrated, the outer surface 80 of the syringe body has a slight bevel so there is an empty space 82 defined between the heat-conductive template 78 and the outer surface 80 of the syringe body 16. The bevel, and resulting space 82, are not necessarily part of the invention and are for illustrative purposes only. The needle guard 112 shown is the second embodiment illustrated in FIG. 3 and includes shoulder 74, designed to engage with detent 56 on syringe body 16.

FIG. 7 also illustrates a device for heating the template 78, which in this particular instance is a hotplate 84. It will be readily appreciated that the heat-conductive template 78 can be provided as a series of templates in a modular assembly that can sealingly engage with a plurality of needle guards. A plurality of needles and/or syringes can therefore be disabled sequentially, or simultaneously, using the apparatus and method of the invention.

When the elongated chamber of the needle guard of FIG. 7 becomes hot, the heat-labile material melts on both the inner and outer surfaces of the chamber and flows onto the needle, and syringe body, respectively. Subsequent cooling of the needle guard encapsulates the inner sections of the chamber to the needle and the outer sections of the chamber to the syringe body.

A kit for disabling a syringe can include the needle guard of the invention, a heat-conductive template that is constructed and arranged to engage with part of the needle guard in a heat-conductive relationship, and a syringe of the invention. Optionally, the kit can also include a device for heating the template.

In particular, a preferred kit for disabling a syringe can include: (i) a needle guard having an elongated member with a bore for receiving a syringe needle, a surface of the bore supporting a heat-labile material; (ii) a heat-conductive template, as described above, and (iii) a syringe including a hollow syringe body, a plunger operating within the body and a needle protruding from a discharge end of the syringe. The preferred syringe component of the kit has a protruding needle supported on a resilient hub disposed within the hollow syringe body at the discharge end of said syringe. The hub is adapted for movement between a first position, where the hub is constrained at the discharge end, and a second position, where the hub is displaced from the discharge end so that at least a portion of the protruding needle is retracted into the syringe body.

The foregoing description is only illustrative of the principles of the invention. It is to be understood that the invention is not limited to the exact construction as illustrated and described herein. Accordingly, all expedient modifications may be made within the spirit of the invention.

What I claim is:

1. A needle guard comprising:
    an elongated member having a bore adapted to receive a needle, said member having at least a portion thereof formed from a heat-labile material, wherein said member includes a core formed of a material that is not heat-labile, and the portion formed from a heat-labile material includes a layer of heat labile material supported on a first surface of said core.
2. The needle guard of claim 1, wherein said heat-labile material melts at a predetermined temperature.
3. The needle guard of claim 1, wherein said heat-labile material is a polymer selected from the group consisting of polylactic acid, polyglycolic acid, polycaprolactone and copolymers of all the foregoing.
4. The needle guard of claim 1, wherein said member further includes a second layer of heat-labile material disposed on a second surface of said core.
5. The needle guard of claim 1, further comprising a means for supporting said member relative to the needle.
6. The needle guard of claim 5, wherein said means for supporting said member relative to the needle includes a flange extending from an end of said member.
7. The needle guard of claim 4, wherein said core is closed at one end.
8. The needle guard of claim 1, wherein said core is formed of a heat-conductive material.
9. A needle and needle guard assembly comprising: an elongated needle; and a needle guard surrounding at least a part of said elongated needle, said needle guard including a first portion made from a heat-labile material and a second portion made from a non-heat-labile material.
10. A syringe assembly comprising, in combination: a hollow syringe body, a plunger operating within said hollow body, a needle protruding from a discharge end of said syringe body, and a needle guard enclosing at least a portion of said needle, said needle guard containing a heat-labile material, wherein said protruding needle is supported on a resilient hub disposed within said hollow syringe body, said hub adapted for movement between a first position where said hub is located at said discharge end, and a second position where said hub is displaced from said discharge end so that at least a portion of the protruding needle is retracted within the syringe body, and wherein said needle guard is connected to said resilient hub and is retractable into said syringe body when said hub is moved from said first to said second position.
11. The syringe assembly of claim 10, wherein said hollow syringe body includes a detent on an inner surface thereof, the detent located at said discharge end.
12. The syringe assembly of claim 11, wherein said heat-labile material is constructed and arranged to engage with said detent on the inner surface of the hollow syringe body.
13. A kit for disabling a syringe assembly, comprising:
    a needle guard including an elongated member having a bore for receiving a syringe needle, said member further including a layer of heat-labile material supported on a surface of said bore; and
    a heat conductive template for engaging a portion of the needle guard in a heat-conductive relationship.
14. The kit of claim 13, further comprising
    means for heating the template in order to melt said heat-labile material.
15. A needle guard comprising:
    an elongated member having a bore adapted to receive a needle, said member having a first portion formed from a heat-labile material and a second portion formed from a non-heat-labile material.

* * * * *